United States Patent [19]

Katner et al.

[11] 4,075,214
[45] Feb. 21, 1978

[54] PREPARATION OF LEUROSIDINE AND NOVEL LEUROSIDINE 4'-ETHERS AND ESTERS

[75] Inventors: Allen S. Katner; Gerald E. Gutowski; Jean C. Miller, all of Indianapolis, Ind.

[73] Assignee: Eli Lilly and Company, Indianapolis, Ind.

[21] Appl. No.: 687,274

[22] Filed: May 17, 1976

[51] Int. Cl.² .......................................... C07D 471/18
[52] U.S. Cl. ................................ 260/287 B; 424/262
[58] Field of Search ..................................... 260/287 B

[56] References Cited

U.S. PATENT DOCUMENTS 3,205,220  9/1965  Svoboda et al. .................... 424/195

OTHER PUBLICATIONS

Neuss et al., Tetrahedron Letters, No. 9, pp. 811–816, 1967.

*Primary Examiner*—Paul M. Coughlan, Jr.
*Attorney, Agent, or Firm*—James L. Rowe; Everet F. Smith

[57] ABSTRACT

Vincaleukoblastine (VLB, vinblastine) is converted to leurosidine, its 4' epimer, by reaction with thionyl chloride to form a bis-sulfite ester followed by treatment of the bis-sulfite ester with silver perchlorate. The bis-sulfite ester is covertible to novel 4' ethers by treatment with a lower alkanol or 4' esters of leurosidine perchlorate with acetic anhydride.

5 Claims, No Drawings

PREPARATION OF LEUROSIDINE AND NOVEL LEUROSIDINE 4'-ETHERS AND ESTERS

BACKGROUND OF THE INVENTION

Vincoleukoblastine (VLB, vinblastine) was the first of the dimeric indole alkaloids to be used in the treatment of malignancies. The compound is the subject of U.S. Pat. No. 3,097,137, to Beer, Cutts and Noble. The next of the dimeric indole alkaloids to be used in the treatment of malignancies, and in particular of the acute leukemias of childhood, was leurocristine (vincristine)—see U.S. Pat. No. 3,205,220 to Svoboda, Barnes and Armstrong. Also claimed in this latter patent was the dimeric vinca alkaloid, leurosidine, an isomer of VLB. VLB, vincristine, and leurosidine can all be represented by Formula I below as follows:

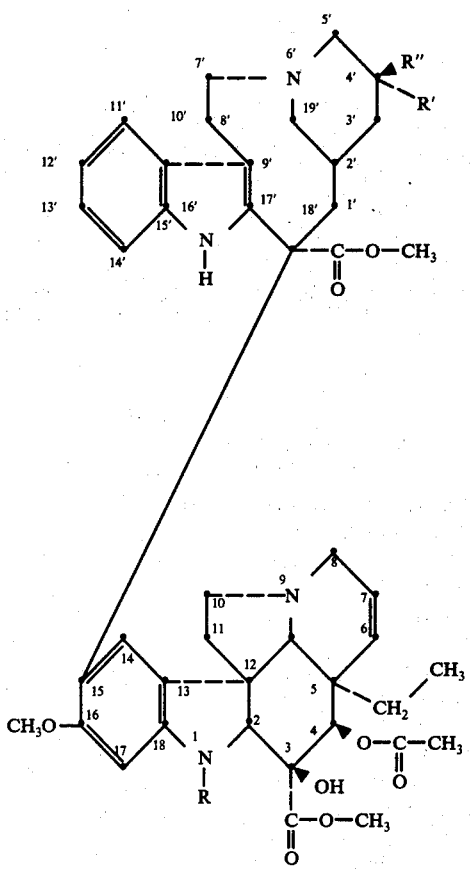

FORMULA I

In Formula I, when R is formyl, R' is ethyl, and R" is hydroxy, the resulting compound is vincristine; when R is methyl, R' is ethyl, and R" is hydroxy, the compound is VLB. Leurosidine, being a C—4' epimer of vinblastine, is represented by Formula I when R is methyl, R' is hydroxy, and R" is ethyl. Originally, leurosidine was thought to have a structure isomeric (rather than epimeric) with VLB in that the hydroxyl group was believed to be at 3' rather than 4'—see Neuss, Huckstep, and Cone, *Tetrahedron Letters*, 811, (1967). More recently, however, Wenkert et al. publishing in *Helvetica Chimica Acta*, 58, 1560 (1975) have shown that leurosidine is not the 3'-hydroxy isomer of VLB but is the 4'epimer having an α-hydroxyl and a β-ethyl group.

Neuss, Huckstep and Cone (loc. cit.) acetylated leurosidine to prepare a 3,4'-diacetate [referred to in Table 1 on page 815 as VRD acetate (tri). A third acetate residue is already present at C—4 in leurosidine]. Table 1 states, however, that the diacetate (4'-acetyl leurosidine) was not prepared; in other words, VRD 3,4,4'-triacetate was not treated according to the procedure of Hargrove, *Lloydia*, 27, 340 (1964) to remove the C—3 acetate to prepare leurosidine 4'-acetate.

Leurosidine, like vincristine, is obtained only in very small quantities by the extraction of leaves of *Vinca rosea*. Leurosidine has a broad anti-tumor spectrum in transplanted tumors in mice. Of particular interest is a number of definite survivors in mice innoculated with P-1534 leukemia cells. A clinical trial of leurosidine in humans, however, yielded no positive results and there was some evidence of toxicity. The clinical trial was limited by the small amount of drug available. The activity of leurosidine against P-1534 leukemia in mice would, however, have been of sufficient interest to prompt the preparation of leurosidine derivatives having a decreased toxicity had a sufficient supply of the drug then been available.

It is an object of this invention to provide a simple and convenient route for the preparation of leurosidine from the more abundant vinca alkaloid, VLB.

SUMMARY OF THE INVENTION

In fulfillment of the above and other objects, this invention provides a method for the epimerization of VLB at C—4' to yield leurosidine, which method comprises reacting VLB (Formula II below when R' is ethyl and R" is hydroxy)

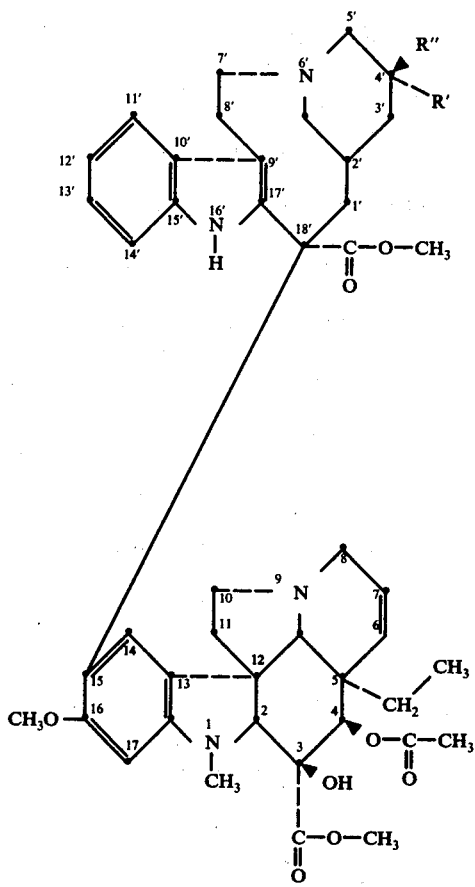

FORMULA II with thionyl chloride in the presence of pyridine to yield the intermediate bis-sulfite ester of Formula III.

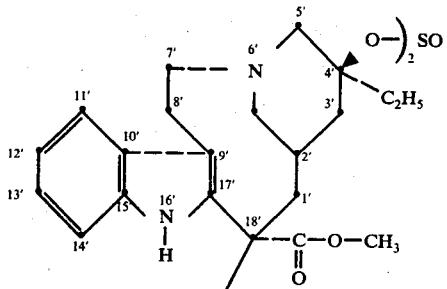

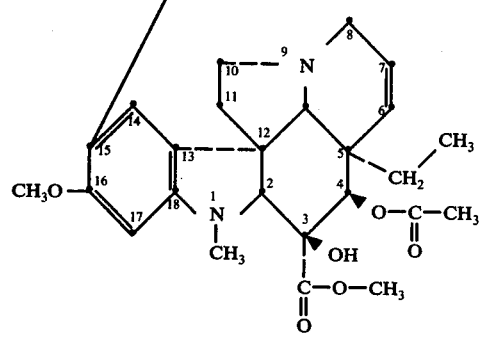

FORMULA III

Treatment of this bis-sulfite ester with silver perchlorate in an aqueous solvent yields leurosidine as the perchlorate salt. Leurosidine free base is recovered from the salt by conventional procedures including suspension of the water-insoluble salt in water, addition of alkali to convert the salt to the free base with concurrent extraction of the free base into a water immiscible solvent. Evaporation of the solvent yields leurosidine. Treatment of the intermediate bisulfite ester with silver perchlorate in methanol yields C—4' methoxy leurosidine (Formula II wherein R' is $OCH_3$ and R" is ethyl). In addition, leurosidine perchlorate can be transformed to the C—4' acetate with acetic anhydride in the presence of pyridine.

In carrying out the first step of the above conversion; i.e., the preparation of the bis-sulfite ester, a large excess of thionyl chloride, for example a 10–20 fold excess, is employed. The solvent of choice for this reaction is pyridine although other aromatic tertiary amine bases such as α-picoline can be used. In the second step of the reaction sequence; i.e., the hydrolysis of the bis-sulfite ester, silver perchlorate in a slight excess (10 percent) is employed in an aqueous solvent system. The preferred solvent is a mixture of water and tetrahydrofuran (THF). Other water miscible solvents which do not react with silver perchlorate such as dioxane can be used in place of THF in the above hydrolytic system.

If a compound according to Formula II above wherein R" is lower alkoxy is to be prepared by reacting the bis-sulfite ester with a lower alkanol such as methanol, ethanol, or propanol, a non-reactive water immiscible solvent such as methylene dichloride can be employed with the lower alkanol.

The preparation of leurosidine 4'-acetate is carried out utilizing standard synthetic procedures such as acetic anhydride or acetyl chloride or a mixed anhydride of acetic and trifluoroacetic acids in the presence of pyridine as a solvent or with acetyl chloride in a non-reactive solvent using pyridine as a catalyst, but the reaction is carried out at low temperature (−10° to 10° C.) so as to minimize acetylation of the 3-hydroxyl. Acetylation at C—3 might be expected from the work of Hargrove, *Lloydia*, 27, 340 (1964). Alternatively, treatment of VLB 4'-bis-sulfite ester with silver acetate in acetic acid also yields leurosidine 4'-acetate without any concomitant acetylation at C-3.

This invention is further illustrated by the following specific examples.

Example 1

PREPARATION OF VLB 4'-BISULFITE ESTER

A solution of 62 g. of VLB was prepared in 700 ml. of anhydrous pyridine. The solution was cooled to a temperature in the range of −15 to −8° C. 19 ml. of thionyl chloride previously purified by distillation were added in dropwise fashion over a 15 minute period while the temperature was maintained in the above range. The reaction mixture stirred in the same temperature range for an additional two hours and was then quenched in about 5 liters of an ice-water mixture. The reaction product comprising VLB 4'-bis-sulfite ester was collected by filtration and chromatographed over 600 g. of fluorosil, employing an ethylacetate-chloroform solvent mixture as the eluting agent. Fractions shown to contain bis-sulfite ester were combined and the solvent evaporated therefrom in vacuo. The resulting residue was recrystallized from a methylene dichloridemethanol solvent mixture to yield about 10 g. of VLB 4'-bis-sulfite.

EXAMPLE 2

PREPARATION OF LEUROSIDINE

A suspension of 2.0 g. of VLB 4'-bis-sulfite ester in 100 ml. of THF was prepared. A solution of 560 mg. of silver perchlorate dissolved in 25 ml. of water was added thereto. After stirring the resulting mixture for about 4.5 hours, thin-layer chromatography showed that the starting bis-sulfite ester had been entirely converted into equal quantities of leurosidine and of an unknown material. Volatile constituents were removed from the reaction mixture in vacuo and the aqueous solution remaining was partitioned with ethyl acetate. Filtration of the two layers yielded about 980 g. of a white solid comprising leurosidine perchlorate, a high melting, water insoluble white solid.

Leurosidine is isolated from the perchlorate salt by conventional methods, as for example, by the procedure used to obtain leurosodine base from its sulfate salt. In such a procedure, a suspension of leurosidine perchlorate in water is contacted with aqueous alkali thereby forming leurosidine free base is which is extracted into a water-immiscible solvent such as benzene. Leurosidine free base obtained by evaporation of the benzene solvent. It is recrystallized from methanol or ethanol.

EXAMPLE 3

PREPARATION OF 4'-METHOXY LEUROSIDINE

Following the procedure of Example 2, 207.1 mg. of VLB 4'-bis-sulfite ester were suspended in about 100 ml. of methanol. Addition of about 25 ml. of methylene dichloride yielded a solution. 57 mg. of silver perchlorate were added and the resulting mixture stirred at ambient temperature for about 12 hours. Thin-layer chromatography indicated a single-spot. The solvent was removed in vacuo and the residue redissolved in methanol. Isopropanol was added and a white solid comprising 4'-methoxy leurosidine perchlorate precipitated, which solid was separated by filtration. The perchlorate salt melted at about 260° C. 4'-methoxy leurosidine is recovered from the perchlorate salt neutralization with base, extraction of base-insoluble 4'-methoxy leurosidine into a water-immiscible solvent followed by evaporation of the solvent and recrystallization of the resulting residue from methanol.

EXAMPLE 4

PREPARATION OF LEUROSIDINE 4'-ACETATE

A solution was prepared containing 59.2 mg. of leurosidine in 15 ml. of anhydrous pyridine. The solution was cooled to about 15° C. 10 ml. of acetic anhydride were added. The course of the reaction was followed by thinlayer chromatography. The reaction was maintained for 2 hours at 0° C., then allowed to warm to room temperature, maintained for 16 hours at 0°–5° C. and finally for another 1.5 hours at room temperature.

Thin-layer chromatography showed leurosidine 4'-acetate to be the predominant product. The reaction mixture was evaporated to dryness and the residue, comprising leurosidine 4'-acetate formed in the above reaction, was dissolved in methanol. The methanol solution was allowed to stand at room temperature for 15 minutes and the methanol was then removed therefrom by evaporation. This last procedure was repeated. The residue finally obtained was then dissolved in water to which had been added several drops of 1N aqueous hydrochloric acid. The acidic solution was made basic with 14 N ammonium hydroxide and leurosidine 4'-acetate, being insoluble in the aqueous base, separated. Three-fold extraction of the aqueous mixture with methylene dichloride removed the separated leurosidine 4'-acetate. The methylene dichloride extracts were combined, the solvent removed thereform by evaporation in vacuo and dried. A residue of 57.5 mg. of leurosidine 4'-acetate which melted with decomposition at about 133° C. was obtained. Mass spectrum: m/e = 868, 862, 852, 850, 820, 792 and 3, 734, 631, and 3, 469, 351, 282, 135 and 6; nmr (CDCl$_3$). δ 1.94 and 2.10 (acetate), δ 2.72 (N-methyl), δ 3.605 and 3.80 (ester methyls).

The above reaction was repeated with leurosidine obtained from the perchlorate salt according to Example 1 above by dissolving 102.9 mg. of leurosidine thus obtained in 20 ml. of pyridine at 0° C. 10 ml. of acetic anhydride were added. A mixture of leurosidine 4'-acetate and leurosidine 3,4'-diacetate was obtained. The 4'-acetate and 3,4'-diacetate were separated by chromatography.

EXAMPLE 5

ALTERNATE PREPARATION OF LEUROSIDINE ACETATE

A reaction mixture containing 400 mg. of VLB 4'-bis-sulfite ester, 800 mg. of silver acetate and 150 ml. of glacial acetic acid was heated to reflux temperature for 2 hours and was then filtered while still hot. The solvent was removed by evaporation in vacuo and the resulting residue containing leurosidine 4'-acetate formed in the above reaction, was extracted with methylene dichloride. This extract was adsorbed onto preparative TLC plates which were developed with a 3:1 ethylacetate-ethanol solvent mixture. Fractions containing leurosidine 4'-acetate were scraped from the TLC plate and extracted with ethyl acetate. Addition of methanol to this solution caused leurosidine 4'-acetate to crystallize; yield = 93 mg.

A solution of leurosidine 4'-acetate (54 mg.) in 10 ml. of THF and 20 ml. of water was heated to reflux for 2 hours. The reaction mixture was concentrated and addition of methanol to the concentrate yielded crystal (2.6 mg.) of leurosidine acetic acid salt melting with decomposition above 190° C.

Heating leurosidine 4'-acetate in aqueous methanol yields 4'-methoxy leurosidine.

EXAMPLE 6

PREPARATION OF LEUROSIDINE 4'-AZIDE

About 830 mg. of leurosidine bis-sulfite ester from Example 1 were dissolved in anhydrous DMF to which had been added 65 mg. of sodium azide. 207 mg. of silver perchlorate were added as a solid. The reaction mixture was stirred for 2 days but continued to be a heterogenous mixture even after the addition of chloroform in an attempt to solubilize insoluble constituents. The volatile constituents were removed by evaporation in vacuo and the residue partitioned between water and ethyl acetate as in Example 1. Material insoluble in both water and ethyl acetate was separated by filtration. Leurosidine 4'-azide thus isolated was purified by recrystallization. An infrared spectrum of the product showed a medium strength azide band.

Leurosidine is an anti-algal compound (See U.S. Pat. No. 3,205,220). The derivatives of leurosidine provided herein, such as the 4'-methoxy and ethoxy ethers, the 4'-acetate and the 4'-azide also are active as antimicrobial compounds. In addition, these compounds are active as is leurosidine in combating transplanted tumors in mice. Leurosidine has been found to give 80 percent inhibition of the Ridgeway osteogenic sarcoma, for example, at a dose level of 0.4 mg./kg. administered for a 10-day period. Leurosidine 4'-acetate is, of course, readily hydrolyzed to leurosidine both in vitro and in vivo. The 4'-lower alkoxy ethers of leurosidine have a similar action to leurosidine against transplanted tumors in mice. The compounds of this invention would be utilized in cancer therapy in mammals in the same way as are VLB and vincristine; i.e., as solutions available for intravenous administration. The dose levels of leurosidine and its derivatives provided by this invention are somewhat higher than those of VLB.

We claim:

1. A compound of the formula

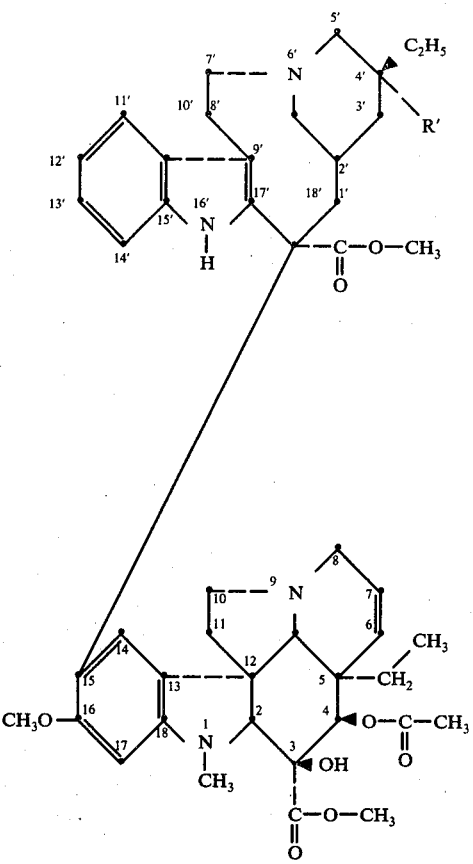

wherein R' is methoxy, ethoxy, propoxy or an azide group.

2. A process for preparing leurosidine and its 4'-lower alkoxy ethers which comprises reacting VLB with thionyl chloride in pyridine to form a 4'-bis-sulfite ester of VLB and then reacting said bis-sulfite ester with silver perchlorate in the presence of water or of a lower alkanol to form a compound of the formula

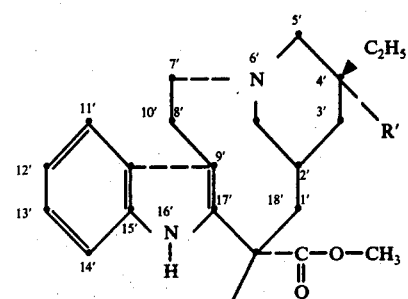
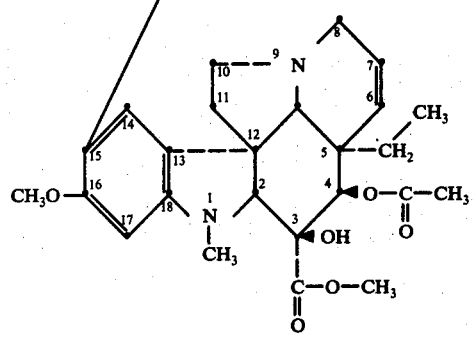
wherein R' is hydroxy, methoxy, ethoxy, or propoxy.
3. A compound according to claim 1, said compound being leurosidine 4'-azide.
4. A compound according to claim 1, said compound being 4'-methoxy leurosidine.
5. VLB 4'-bis-sulfite ester of the formula
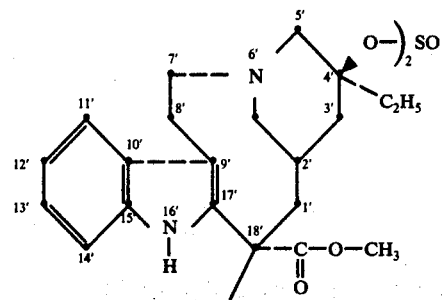
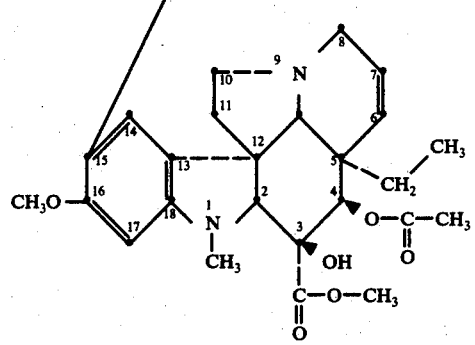
* * * * *